(12) United States Patent
Ferreira et al.

(10) Patent No.: US 10,005,719 B1
(45) Date of Patent: Jun. 26, 2018

(54) METHOD FOR DIRECTED CATALYTIC FUNCTIONALIZATION OF ALCOHOLS

(71) Applicant: The University of Georgia Research Foundation, Inc., Athens, GA (US)

(72) Inventors: Eric Ferreira, Athens, GA (US); Brian J Knight, Gainesville, FL (US); Qiankun Li, Taihe (CN)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days. days.

(21) Appl. No.: 15/088,014

(22) Filed: Mar. 31, 2016

Related U.S. Application Data

(60) Provisional application No. 62/141,093, filed on Mar. 31, 2015.

(51) Int. Cl.
| | | |
|---|---|---|
| C07C 231/12 | (2006.01) | |
| C07C 67/347 | (2006.01) | |
| C07C 29/44 | (2006.01) | |
| C07D 491/048 | (2006.01) | |

(52) U.S. Cl.
CPC ............ *C07C 231/12* (2013.01); *C07C 29/44* (2013.01); *C07C 67/347* (2013.01); *C07D 491/048* (2013.01)

(58) Field of Classification Search
CPC .................................................... C07C 231/12
USPC ........................................................ 546/116
See application file for complete search history.

(56) References Cited

PUBLICATIONS

Li et al. Chemistry—A European Journal (2016), 22(37), 13054-13058.*
Rit et al., "Pd(II)-Catalyzed ortho-C—H Oxidation of Arylacetic Acid Derivatives: Synthesis of Benzofuranones," Org. Lett., 2014, 16: 968-971.
Rit et al., "Reusable directing groups [8-aminoquinoline, picolinamide, sulfoximine] in C(sp3)-H bond acitivation: presnet and future," Tetrahedron, 2015, 71: 4450-4459.
Shabashov and Daugulis, "Auxiliary-Assisted Palladium-Catalyzed Arylation and Alkylation of sp2 and sp3 Carbon-Hydrogen Bonds," J. Am. Chem. Soc., 2010, 132: 3965-3972.
Simmons and Hartwig, "Catalytic funcitonalization of unactivated primary C—H bonds directed by an alcohol," Nature, 2012, 483:70-73.
Simmons and Hartwig, "Iridium-Catalyzed Arene Ortho-Silylation by Formal Hydroxyl-Directed C—H Activation," J. Am. Chem. Soc., 2010, 132: 17092-17095.
Stache et al., "Molecular scaffolds with remote directing groups for selective apalldium-catalyzed C—H bond functionalizations," Chem. Sci., 2012, 3: 1623-1628.
Thompson et al., "Cyclic Ether Synthesis via Palladium-Catalyzed Directed Dehydrogenative Annulation at Unactivated Terminal Positions," J. Am. Chem. Soc., 2015, 137: 11586-11589.
Wan et al., "Cross-Coupling of Remote meta-C—H Bonds Directed by a U-shaped Template," J. Am. Chem. Soc., 2013, 135: 18056-18059.
Wang and Gevorgyan, "General Method for the Synthesis of Salicylic Acids from Phenols through Palladium-Catalyzed Silanol-Directed C—H Carboxylation," Angew. Chem. Int. Ed., 2015, 54: 2255-2259.
Wang and Huang, "Expanding Structural Diversity; Removable and Manipulable Directing Groups for C—H Activation," SYNLETT 2013, 24: 145-149.
Wang et al., "Pd(II)-Catalyzed Hydoxyl-Directed C—H Acivation/C—O Cyclization: Expedient Construction of Dihydrobenzofurans," J. Am. Chem. Soc., 2010, 132: 12203-12205.
Xiao et al., "Pd(II)-Catalyzed C—H Activation/Aryl-Aryl Coupling of Phenol Esters," J. Am. Chem. Soc., 2010, 132: 468-469.
Xu et al., "Diverse sp3 C—H functionalization through alcohol β-sulfonyloxylation," Nat. Chem., 2015, 7: 829-835.
Yang et al., "Pd(II)-Catalyzed meta-C—H Olefination, Arylation, and Acetoxylation of Indolines Using a U-Shaped Template," J. Am. Chem. Soc., 2014, 136: 10807-10813.
Yeung and Dong, "Catalytic Dehydrogenative Cross-Coupling: Forming Carbon-Carbon Bonds by Oxidizing Two Carbon-Hydrogen Bonds," Chem. Rev., 2011, 111: 1215-1292.
Zaitsev et al., "Highly Regioselective Arylation of sp3 C—H Bonds Catalyzed by Palladium Acetate," J. Am. Chem. Soc., 2005, 127: 13154-13155.
Zhang and Spring, "Arene C—H functionalisation using a removable/modifiable or a traceless directing group strategy," Chem. Soc. Rev., 2014, 43: 6906-6918.
Zhang et al., "Palladium-Catalyzed Aromatic C—H Bond Nitration Using Removable Directing Groups: Regiospecific Synthesis of Substituted o-Nitrophenols from Related Phenols," J. Org. Chem, 2014, 79: 11508-11516.
Narasimhan et al., "Evidence in Favor of Lithium-Halogen Exchange Being Faster Than Lithium-Acidic Hydrogen (Deuterium) Exchange," J. Am. Chem. Soc., 1990, 112(11): 4431-4435.
Nandhikonda and Heagy, "Dual Fluorescent N-Aryl-2,3-naphthalimides: applications in Ratiometric DNA Detection and White Organic Light-Emitting Devices," Org. Lett., 2010, 12(21): 4796-4799.
Jnaneshwara et al., "Selenium dioxide: a selective oxidising agent for the functionalisation of quinolines," J. Chem. Res. (S), 2000, 34-35.
Ackermann et al., "Ruthenium-Catalyzed C—H Bond Arylations of Arenes Bearing Removable Directing Groups via Six-Membered Ruthenacycles," Organic Letters, 2012, 14(4): 1154-1157.
Alberico et al., "Aryl-Aryl Bond Formation by Transition-Metal-Catalyzed Direct Arylation," Chem. Rev., 2007, 107: 174-238.
Alsters et al., "Rigid Five- and Six-Membered C,N,N'-Bound Aryl, Benzyl, and Alkyl Organopalladium Complexes: sp2 vs sp3 C—H Activation during Cyclopalladation and Palladium(IV) Intermediates in Oxidative Addition Reactions with Dihalogens and Alkyl Halides," Organometallics, 1993, 12: 1831-1844.
Arockiam et al., "Ruthenium(II)-Catalyzed C—H Bond Activation and Functionalization," Chem. Rev., 2012, 112:5879-5918.
Ashenhurst JA, "Intermolecular oxidative cross-coupling of arenes," Chem. Soc. Rev., 2010, 39: 540-548.

(Continued)

*Primary Examiner* — Nizal S Chandrakumar
(74) *Attorney, Agent, or Firm* — Thomas | Horstemeyer, LLP

(57) ABSTRACT

A method of preparing ortho-alkenyl and ortho-acetyl benzylic alcohols is disclosed.

12 Claims, 12 Drawing Sheets

(56) References Cited

PUBLICATIONS

Bedford et al., "The Catalytic Intermolecular Orthoarylation of Phenols," Angew. Chem. Int. Ed., 2003, 42(1): 112-114.

Breit and Rousseau, "Removable Directing Groups in Organic Synthesis and Catalysis," Angew. Chem. Int. Ed., 2011, 50: 2450-2494.

Carrión and Cole-Hamilton, "Halide-free ethylation of phenol by multifunctional catalysis using phosphinite ligands," Chem. Commun., 2006, 4527-4529.

Chen and Shi, "Sulfonamide-Promoted Palladium(II)-Catalyzed Alkylation of Unactivated Methylene C(sp3)-H Bonds with Alkyl Iodides," Angew. Chem. Int. Ed., 2014, 53: 11950-11954.

Chu et al., "Palladium(II)-Catalyzed Ortho Arylation of 2-Phenoxypyridines with Potassium Aryltrifluoroborates via C—H Functionalization," Organometallics, 2010, 29: 4058-4065.

Chu et al., "Remote Meta-C—H Activation Using a Pyridine-Based Template: Achieving Site-Selectivity via the Recognition of Distance and Geometry," ACS Cent. Sci., 2015, 1: 394-399.

Colby et al., "Rhodium-Catalyzed C—C Bond Formation via Heteroatom-Directed C—H Bond Activation," Chem. Rev., 2010: 624-655.

Cong et al., "2-Pyridylmethyl ether: a readily removable and efficient directing group for amino acid ligand accelerated orth-C—H olefination of phenols," ChemComm, 2013, 49: 662-664.

Corbet and De Campo, "8-Aminoquinoline: A Powerful Directing Group in Metal-Catalyzed Direct Functionalization of C—H Bonds," Angew. Chem. Int. Ed., 2013, 52: 9896-9898.

Dai et al., "Pd(II)-Catalyzed ortho- or meta-C—H Olefination of Phenol Derivatives," J. Am. Chem. Soc., 2013, 135: 7567-7571.

Deng and Yu, "Remote meta-C—H Olefination of Phenylacetic Acids Directed by a Versatile U-Shaped Template," Angew. Chem. Int. Ed., 2015, 54: 888-891.

Engle et al., "Ligand-Accelerated C—H Activation Reactions: Evidence for a Switch of Mechanism," J. Am. Chem. Soc., 2010, 132: 14137-14151.

Engle et al., "Ligand-Accelerated Cross-Coupling of C(sp2)-H Bonds with Arylboron Reagents," J. Am. Chem. Soc., 2011, 133: 18183-18193.

Ferreira EM, "A urrogate for selectivity," Nat. Chem., 2014, 6: 94-96.

Fraunhoffer and White, "syn-1,2-Amino Alcohols via Diastereoselective Allylic C—H Amination," J. Am. Chem. Soc., 2007, 129: 7274-7276.

Gormisky and White, "Synthetic Versatility in C—H Oxidation: A Rapid Approach to Differentiated Diols and Pyrans from Simple Olefins," J. Am. Chem. Soc., 2011, 133: 12584-12589.

Guo et al., "Direct ortho-C—H Functionalization of Aromatic Alcohols Masked by Acetone Oxime Ether via exo-Palladacycle," Org. Lett., 2015, 17: 1802-1805.

Guo et al., "Palladium(II)-Catalyzed Acetoxime Directed ortho-Arylation of Aromatic Alcohols," Chem. Eur. J., 2015, 21: 17474-17478.

Huang et al., "Silanol: A Traceless Directing Group for Pd-Catalyzed o-Alkenylation of Phenols," J. Am. Chem. Soc., 2011, 133: 12406-12409.

Huang et al., "Synthesis of Catechols from Phenols via Pd-Catalyzed Silanol-Directed C—H Oxygenation," J. Am, Chem. Soc., 2011, 133: 17630-17633.

Hussain and Singh, "Synthesis of Biaryls through Aromatic C—H Bond Activation: A Review of Recent Developments," Adv. Synth. Catal., 2014, 356: 1661-1696.

Kandukuri et al., "Diastereotopic Group Selection in Hydroxy-Directed Intramolecular C—H Alkenylation of Indole under Oxidative Palladium(II) Catalysis," Adv. Synth. Catal., 2014, 356: 1597-1609.

Kim et al., "Pd-catalyzed oxidative acylation of 2-phenoxypyridines with alcohols via C—H bond activation," Tetrahedron, 2013, 69: 6552-6559.

Knight et al., "The design of a readily attachable and cleavable molecular scaffold for ortho-selective C—H alkenylation of arene alcohols," Chem. Sci., 2016, 7: 1982-1987.

Lee et al., "Meta-Selective C—H Functionlization Using a Nitrile-Based Directing Group and Cleavable Si-Tether," J. Am. Chem. Soc., 135: 18778-18781.

Leow et al., "Activation of remote meta-C—H bonds assisted by an end-on template," Nature, 2012, 486: 518-522.

Lewis and Smith, "Catalytic C—C Bond Formation via Ortho-Metalated Complexes," J. Am. Chem. Soc., 1986, 108(10): 2728-2735.

Lewis et al., "Preagostic Rh—H Interactions and C—H Bond Functionalization: A Combined Experimental and Theoretical Investigation of Rhodium (I) Phosphinite Complexes," Organometallics, 2005, 24: 5737-5746.

Li et al., "Iridium-Catalyzed Regioselective Silylation of Secondary Alkyl C—H Bonds for the Synthesis of 1,3-Diols," J. Am. Chem. Soc., 2014, 136: 6586-6589.

Liu et al., "Ni(II)/BINOL-Catalyzed alkenylation of unactivated C(sp3)-H bonds," Chem. Commun., 2015, 51: 7899-7902.

Liu et al., "Palladium-Catalyzed Oxidative Olefination of Phenols Bearing Removable Directing Groups under Molecular Oxygen," J. Org. Chem., 2014, vol. 79: 1521-1526.

Lu et al., "Hydroxyl-directed C—H carbonylation enabled by mono-N-protected amino acid ligands: An expedient route to 1-isochromanones," Chem. Sci., 2011, 2: 967-971.

Lu et al., "Pd(II)-Catalyzed Hydroxyl-Directed C—H Olefination Enabled by Monoprotected Amino Acid Ligands," J. Am. Chem. Soc., 2010, 132: 5916-5921.

Lyons and Sanford, "Palldium-Catalyzed Ligand-Dreicted C—H Functionalization Reactions," Chem. Rev., 2010, 110: 1147-1169.

Ma and Ackermann, "Ruthenium(II)-Catalyzed C—H Alkenylations of Phenols with Removable Directing Groups," Chem. Eur. J., 2013, 19: 13925-13928.

McGlacken and Bateman, "Recent advances in aryl-aryl bond formation by direct arylation," Chem. Soc. Rev., 2009, 38: 2447-2464.

Mo et al., "Alcohols or Masked Alcohols as Directing Groups for C—H Bond Functionalization," Chem. Lett., 2014, 43: 264-271.

Morimoto et al., "Synthesis of Isochromene and Related Derivatives by Rhodium-Catalyzed Oxidative Coupling of Benzyl and Allyl Alcohols with Alkynes," J. Org. Chem., 2011, 76: 9548-9551.

Nakanowatari and Ackermann, "Ruthenium(II)-Catalyzed Synthesis of Isochromenes by C—H Activation with Weakly Coordinating Aliphatic Hydroxyl Groups," Chem, Eur. J., 2014, 20: 5409-5413.

Nourry et al., "Synthesis of an analogue fo lavendamycin and of conformationally restricted derivatives by cyclization via a hemiaminal intermediate," Tetrahedrom Letters, 2007, 48: 6014-6018.

Oi et al., "Rhodium-HMPT-catalyzed direct ortho arylation of phenols with aryl bromides," Tetrahedron Letters, 2003, 44: 8665-8668.

Pascual et al., "Palladium catalyzed arylation for the synthesis of polyarenes," Org. Biomol. Chem., 2007, 5: 2727-2734.

Ren et al., "Catalytic Functionalization of Unactivated sp3 C—H Bonds via exo-Directing Groups: Synthesis of Chemically Differentiated 1,2-Diols," J. Am. Chem. Soc., 2012, 134: 16991-16994.

Ren et al., "Catalytic Ortho-Acetoxylation of Masked Benzyl Alcohols via an Exo-Directing Mode," Org. Lett., 2015, 17: 2696-2699.

Rice and White, "Allylic C—H Amination for the Preparation of syn-1,3-Amino Alcohol Motifs," J. Am. Chem. Soc., 2009, 131:11707-11711.

* cited by examiner

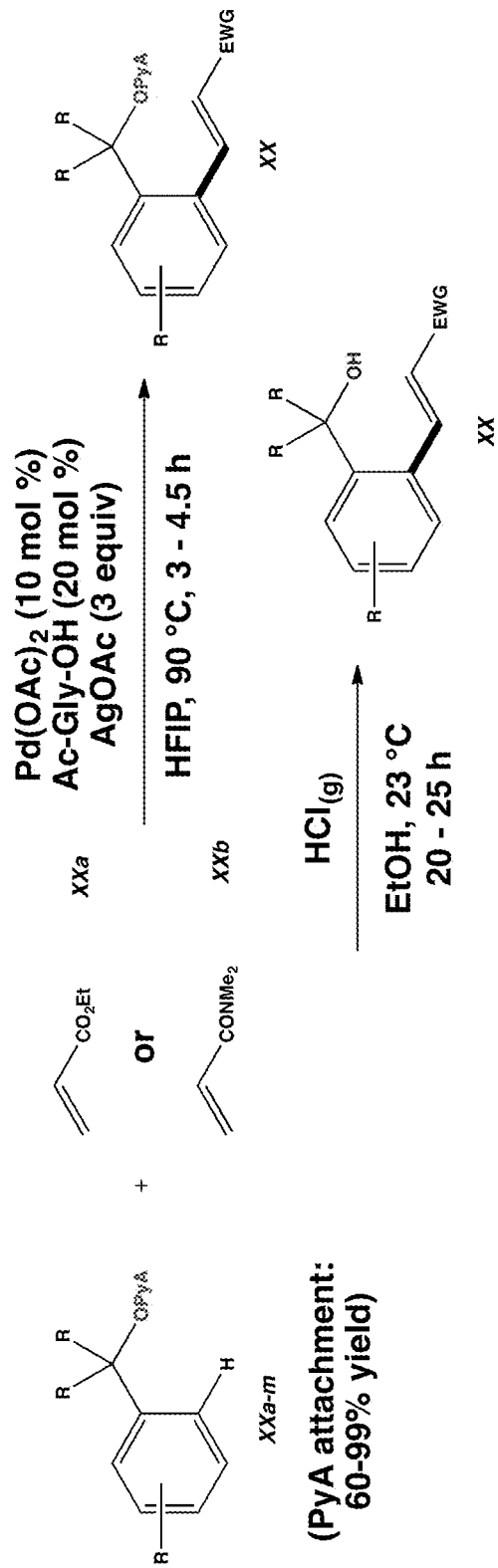

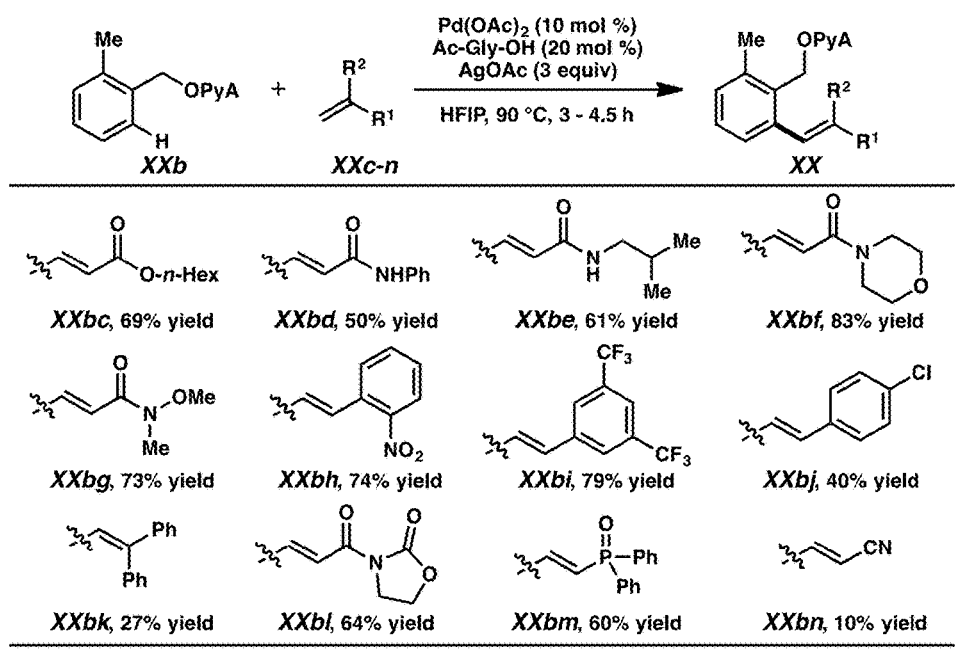
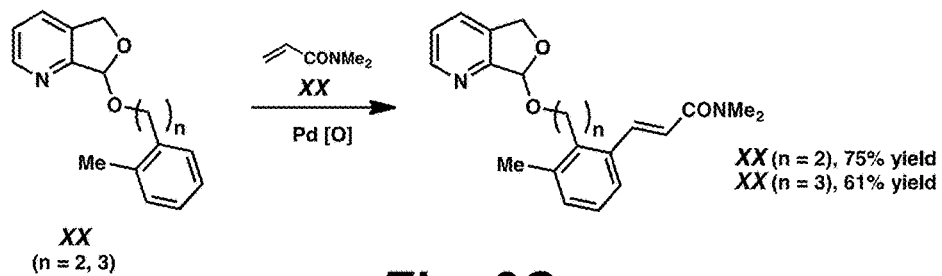
Fig. 6C

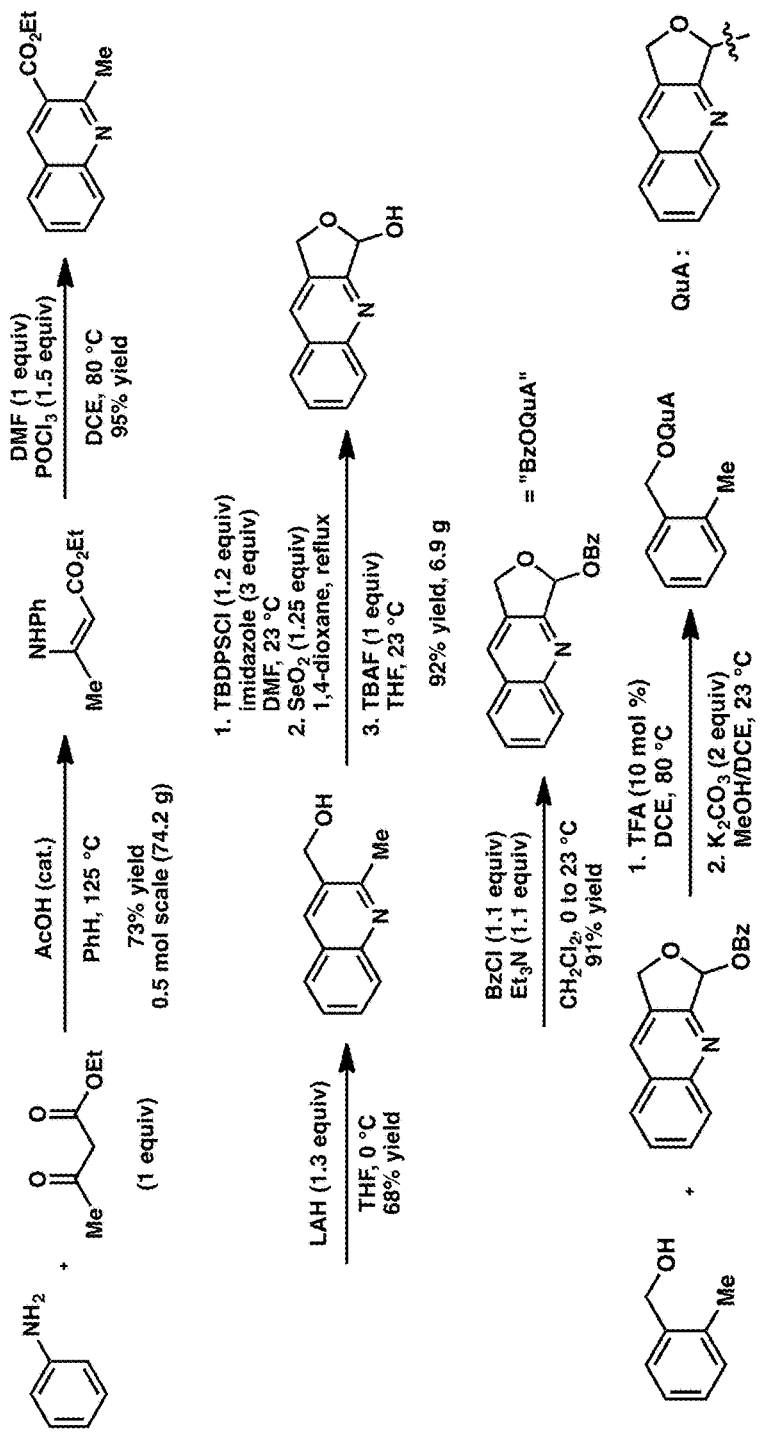

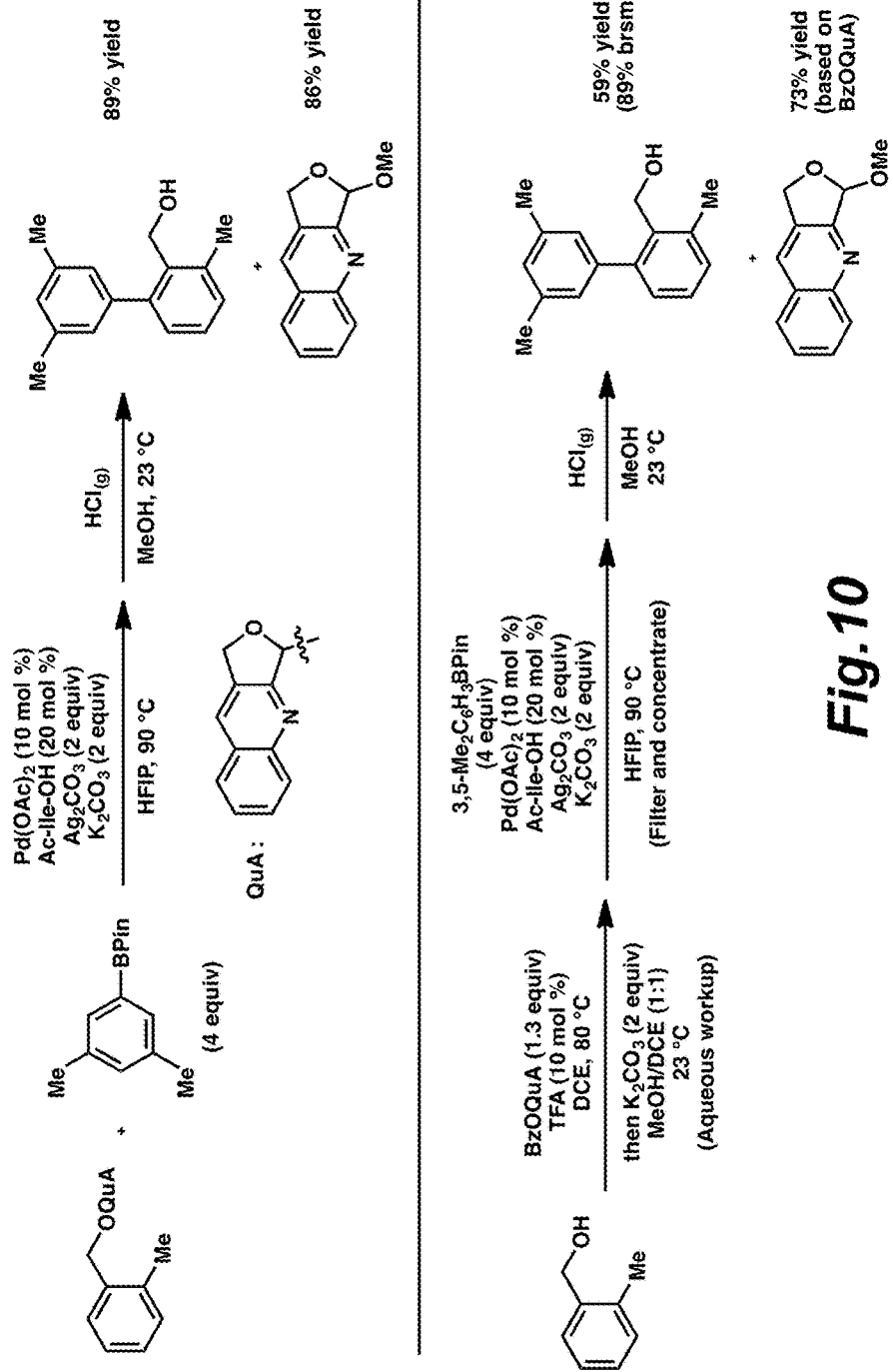

METHOD FOR DIRECTED CATALYTIC FUNCTIONALIZATION OF ALCOHOLS

CROSS-REFERENCE TO RELATED APPLICATIONS

This application claims the benefit of and priority to U.S. Provisional Application Ser. No. 62/141,093, having the title "METHOD FOR DIRECTED CATALYTIC FUNCTIONALIZATION OF ALCOHOLS", filed on Mar. 31, 2015, the disclosure of which is incorporated herein by reference in its entirety.

STATEMENT REGARDING FEDERALLY SPONSORED RESEARCH OR DEVELOPMENT

This invention was made with Government support under contract NSF-CHE-1339674 awarded by the National Science Foundation and the Environmental Protection Agency. The Government has certain rights in the invention.

BRIEF SUMMARY

The presently disclosed embodiments, as well as features and aspects thereof, are directed towards a process comprising reacting an alcohol, e.g., a benzylic alcohol of formula I:

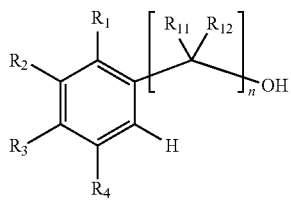

wherein $R_1$, $R_2$, $R_3$ and $R_4$ are independently selected from the group consisting of hydrogen, halogen, alkyl, and aryl; or $R_1$ and $R_2$, or $R_2$ and $R_3$, or $R_3$ and $R_4$ may independently together form an aryl ring;

each $R_{11}$ and $R_{12}$ is independently selected from the group consisting of hydrogen and alkyl;

and n is 1, 2, or 3;

with an acetal of formula II:

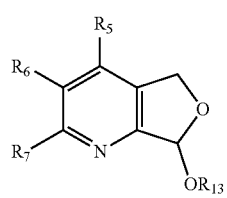

wherein $R_5$, $R_6$, and $R_7$ are independently selected from the group consisting of hydrogen, halogen, and alkyl; or $R_6$ and $R_7$ may together form an aryl ring; and $R_{13}$ is alkyl; to provide the compound of formula III:

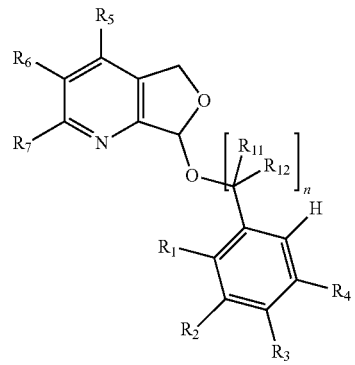

wherein $R_1$, $R_2$, $R_3$, $R_4$, $R_5$, $R_6$, $R_7$, $R_{11}$, $R_{12}$, and n are as recited above;

and reacting the compound of formula III with the unsaturated compound of formula IV:

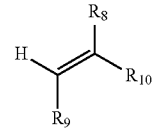

wherein $R_8$ and $R_9$ are independently selected from the group consisting of hydrogen and alkyl; and $R_{10}$ is selected from the group consisting of cyano, nitro, CHO, CO(alkyl), COO(alkyl), CON $H_2$, CONH(alkyl), CON(alkyl)$_2$, wherein each alkyl is selected independent of another alkyl, and aryl; in the presence of a transition metal catalyst, and optionally in the presence of a ligand, and optionally in the presence of a silver salt, and optionally in the presence of a base to provide the compound of formula V:

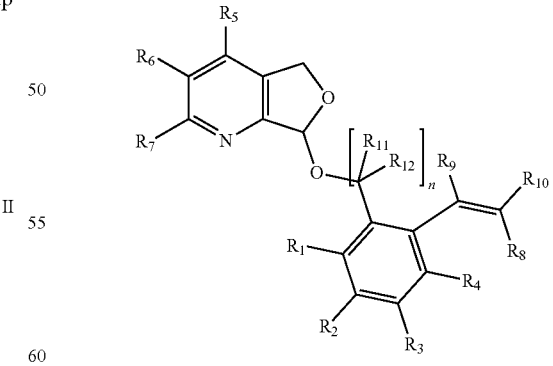

wherein $R_1$, $R_2$, $R_3$, $R_4$, $R_5$, $R_6$, $R_7$, $R_8$, $R_9$, $R_{10}$, $R_{11}$, $R_{12}$, and n are as recited above;

wherein the compound of formula V is reacted with an acid and an alcohol of formula $R_{13}OH$ to provide a) the compound of formula VI:

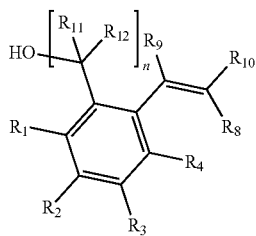

VI wherein $R_1$, $R_2$, $R_3$, $R_4$, $R_8$, $R_9$, $R_{10}$, $R_{11}$, $R_{12}$, and n are as recited above; and b) the compound of formula II.

The presently disclosed embodiments, as well as features and aspects thereof, are directed towards a process comprising reacting an alcohol, e.g., a benzylic alcohol of formula I:

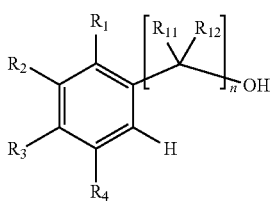

I wherein $R_1$, $R_2$, $R_3$ and $R_4$ are independently selected from the group consisting of hydrogen, halogen, alkyl, and aryl; or $R_1$ and $R_2$, or $R_2$ and $R_3$, or $R_3$ and $R_4$ may independently together form an aryl ring;
each $R_{11}$ and $R_{12}$ is independently selected from the group consisting of hydrogen and alkyl; and
n is 1, 2, or 3;
with an acetal of formula II:

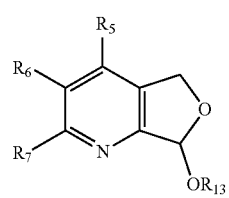

II wherein $R_5$, $R_6$, and $R_7$ are independently selected from the group consisting of hydrogen, halogen, and alkyl; or $R_6$ and $R_7$ may together form an aryl ring; and $R_{13}$ is alkyl; to provide the compound of formula III:

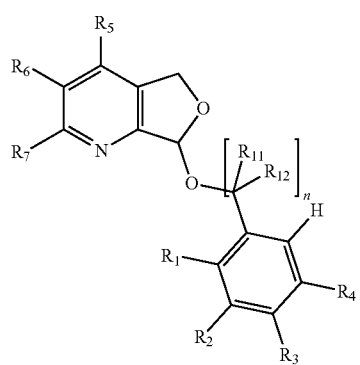

III wherein $R_1$, $R_2$, $R_3$, $R_4$, $R_5$, $R_6$, $R_7$, $R_{11}$, $R_{12}$, and n are as recited above;
and reacting the compound of formula III with a compound of formula IVa:

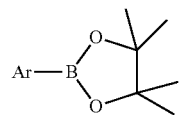

IVa in the presence of a transition metal catalyst, and optionally in the presence of a ligand, and optionally in the presence of a silver salt, and optionally in the presence of a base to provide the compound of formula Va:

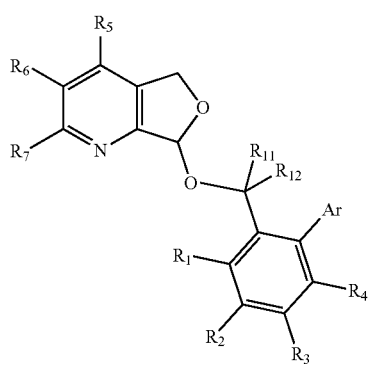

Va wherein $R_1$, $R_2$, $R_3$, $R_4$, $R_5$, $R_6$, $R_7$, $R_{11}$, $R_{12}$, and n are as recited above;
wherein the compound of formula Va is reacted with an acid and an alcohol of formula $R_{13}OH$ to provide a) the compound of formula VIa:

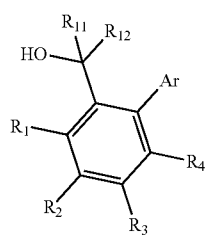

VIa wherein $R_1$, $R_2$, $R_3$, $R_4$, $R_{11}$, $R_{12}$, and n are as recited above; and b) the compound of formula II.

The present embodiments also include the compound of formula II, the compound of formula III, the compound of formula V, the compound of formula Va, the compound of formula VI, and the compound of formula VIa.

BRIEF DESCRIPTION OF THE FIGURES

FIGS. 6A-6C illustrates Scheme 6a.

FIG. 7 illustrates Scheme 7.
FIG. 8 illustrates Scheme 7a.
FIG. 10 illustrates Scheme 8.

DETAILED DESCRIPTION

Figure 1:
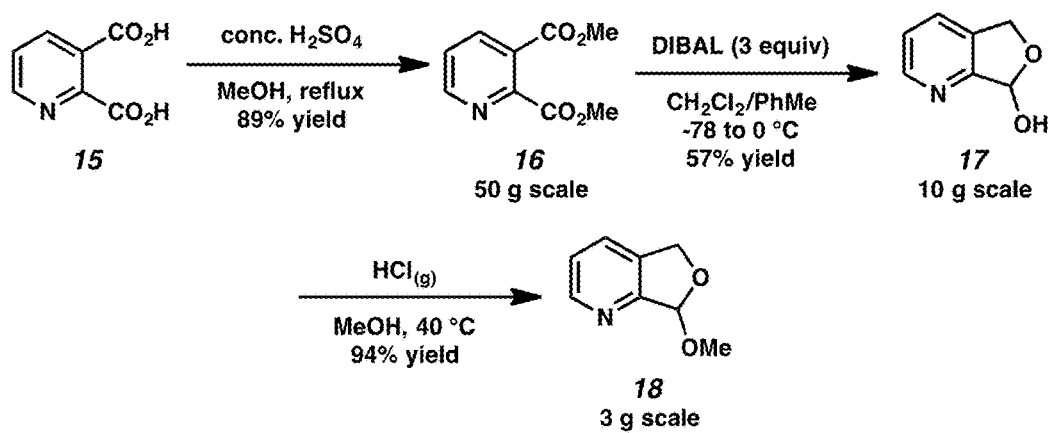
FIG. 1 illustrates Scheme 1.

Aspects, features and advantages of several exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute terms such as, for example, "will," "will not," "shall," "shall not," "must" and "must not" are not meant to limit the scope of the present invention as the embodiments disclosed herein are merely exemplary.

The word "exemplary" is used herein to mean "serving as an example, instance, or illustration." Any aspect described herein as "exemplary" is not necessarily to be construed as exclusive, preferred or advantageous over other aspects.

Alkyl means $C_1$-$C_{12}$ alkyl, optionally substituted by one or more halogen; or alkyl means $C_1$-$C_6$ alkyl, optionally substituted by one or more halogen; or alkyl means $C_1$-$C_3$ alkyl, optionally substituted by one or more halogen.

Alkyl may be methyl, ethyl, propyl, isopropyl, n-butyl, isobutyl, sec-butyl, each independently and optionally substituted by one or more halogen.

$R_{11}$ and $R_{12}$ may both be hydrogen; or $R_{11}$ is methyl and $R_{12}$ is hydrogen; $R_{11}$ and $R_{12}$ may both be methyl.

Aryl or "Ar" means a carbocyclic or heterocyclic aromatic ring that is optionally substituted or fused with another ring.

Ar in the compounds of formula IVa, Va, and VIa may be substituted by one or more alkyl, O-alkyl, COOalkyl, and/or haloalkyl.

In scheme 7 and 7a, the starting benzyl alcohols may be substituted ortho to the benzylic alcohol by haloalkyl, O-alkyl, nitro, or aryl.

"PyA" and "QuA" are defined in Scheme 5.

Halogen means fluorine, chlorine, bromine or iodine.

Transition metal means Paladium, Rhodium, or Ruthenium. Transition metal catalysts include $Pd(OAc)_2$ or a Rhodium acetate, or salt thereof, or a Ruthenium acetate, or a salt thereof. The amount of the transition metal catalyst may be from about 5 mol % to about 50 mol %, or from about 10 mol % to about 40 mol %, or from about 10 mol % to about 40 mol %, or from about 10 mol % to about 30 mol %.

In an embodiment, the process may further comprise a metal catalyst ligand. The ligand may be carboxylic acid, a peptide, e.g., a dipeptide or tripeptide with a carboxylic acid functional group. Examples of a ligand include N-acetyl-isoLeucine (Ac-Ile-OH, CAS Reg. No. 3077-46-1); N-acetyl-tert-butylleucine (Ac-tert-Leu-OH); and N-acetyl glycine (Ac-Gly-OH, CAS Reg, No. 543-24-8). The amount of the ligand may be from about 5 mol % to about 50 mol %, or from about 10 mol % to about 40 mol %, or from about 20 mol % to about 40 mol %, or from about 20 mol % to about 30 mol %.

In an embodiment, the process may further comprise a silver salt, e.g., silver carbonate. The amount of the silver salt may be from about 0.1 to about 5 equivalents, or from about 0.5 to about 4 equivalents, or from about 1 to about 4 equivalents. The process comprising the transition metal may be effected in a fluorinated solvent, e.g., 1,1,1,3,3,3-hexafluoro-2-propanol. The process may be effected at a temperature of from ambient temperature, to about the boiling point of the solvent.

The term "rsm" means recovered starting material.

EXAMPLES

Example 1

Synthesis of Molecular Scaffold of Formula 18:

As shown in Scheme 1 (FIG. 1), pyridine 2,3-dicarboxylic acid was converted to the corresponding diester by esterification in acid. Controlled reduction with diisobutyl aluminum hydride provided hemiacetal 17. Reaction of hemiacetal 17 with gaseous hydrogen chloride in methanol provided the compound of formula 18.

Example 2

Figure 2A:
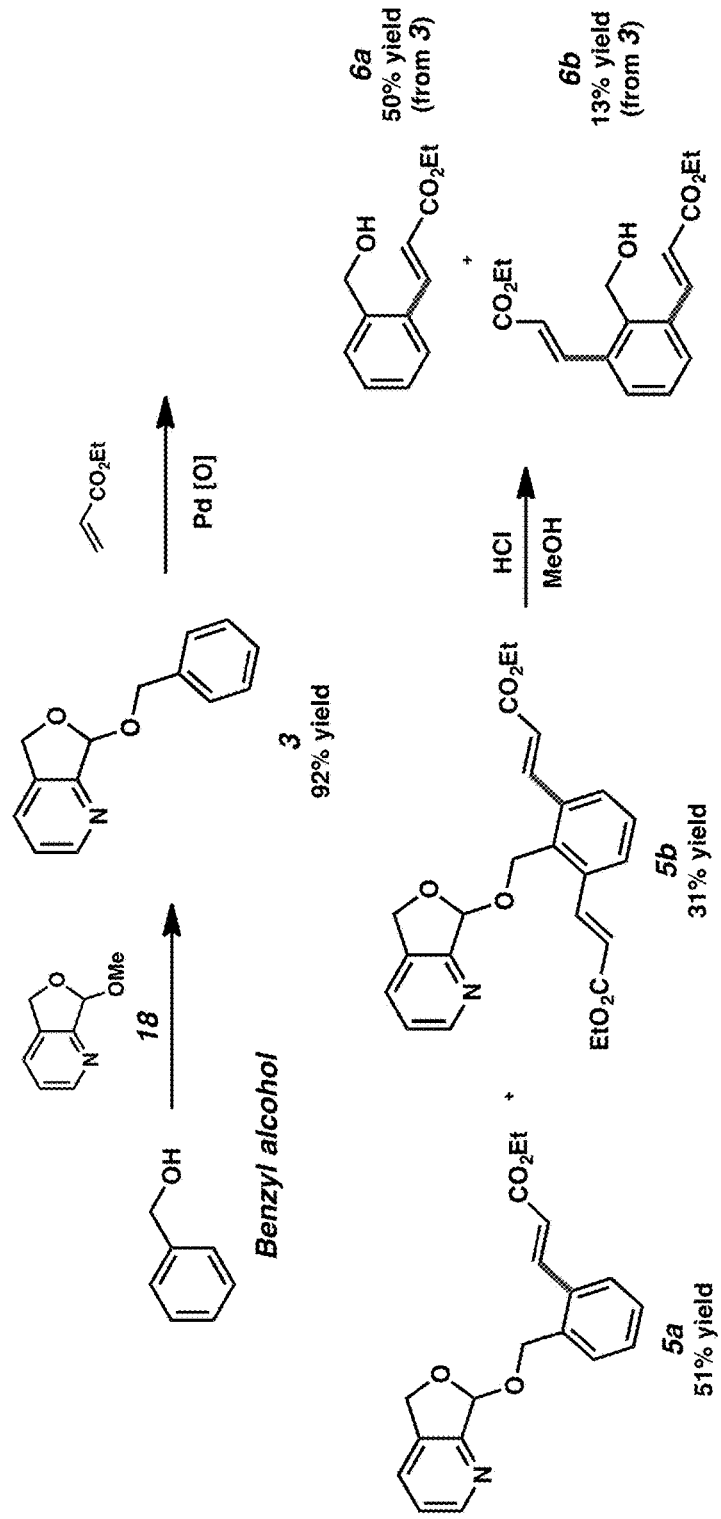
FIGS. 2A and 2B illustrate Scheme 2.
Figure 2B:
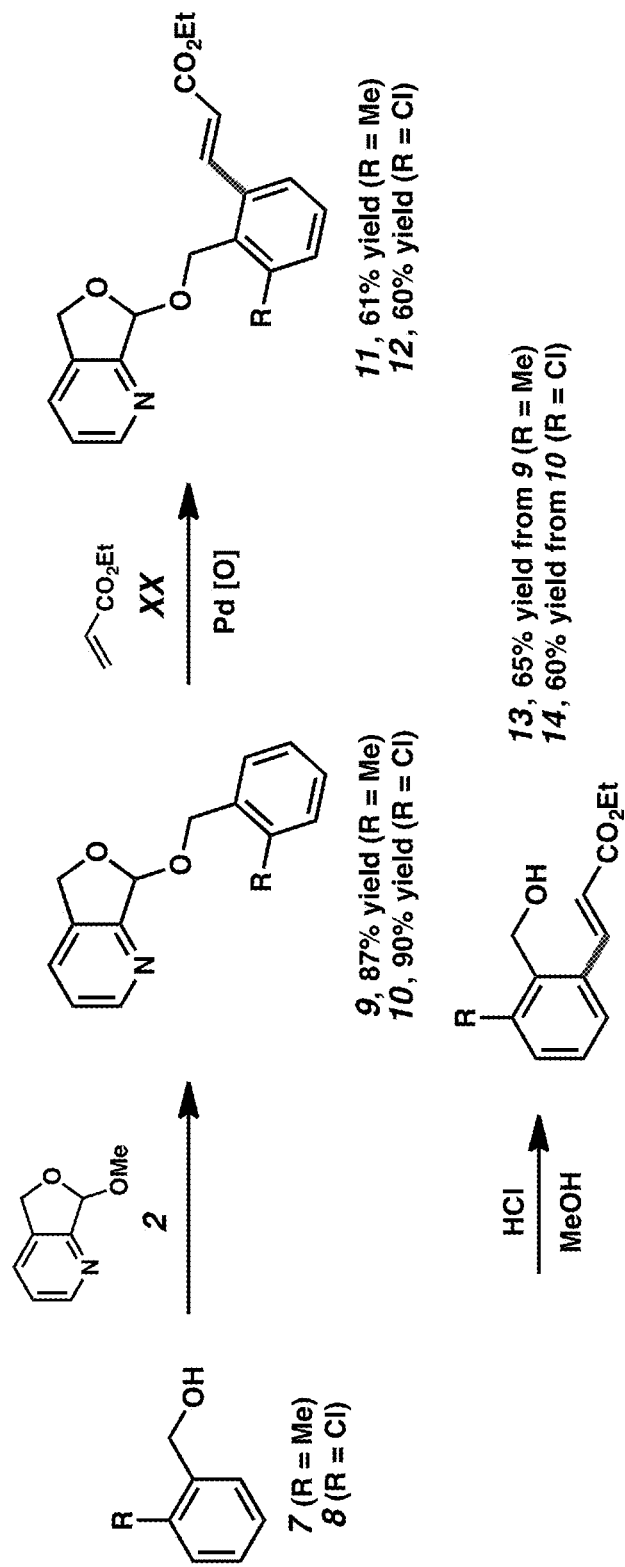

Use of Molecular Scaffold 18 to Functionalize Benzylic Alcohols:

As shown in Scheme 2 (FIG. 2), compound 2 was reacted with benzyl alcohol in the presence of 5 Å molecular sieves to provide the acetal 3 in 92% yield. Reaction of acetal 3 with ethyl acrylate in the presence of catalytic $Pd(OAc)_2$, 0.2 molar equivalents N-acetylglycine, and 3 molar equivalents of AgOAc as the oxidant in hexafluoroisopropanol at 90° C. provided mono-substituted adduct 5a and disubstituted adduct 5b. Reaction with methanol and hydrogen chloride provided compounds 6a and 6b. Reaction of 2-chlorobenzyl alcohol (8) and 2-methylbenzyl alcohol (7) under essentially same conditions afford solely the monosubstituted adducts 14 and 13, respectively.

Figure 3:
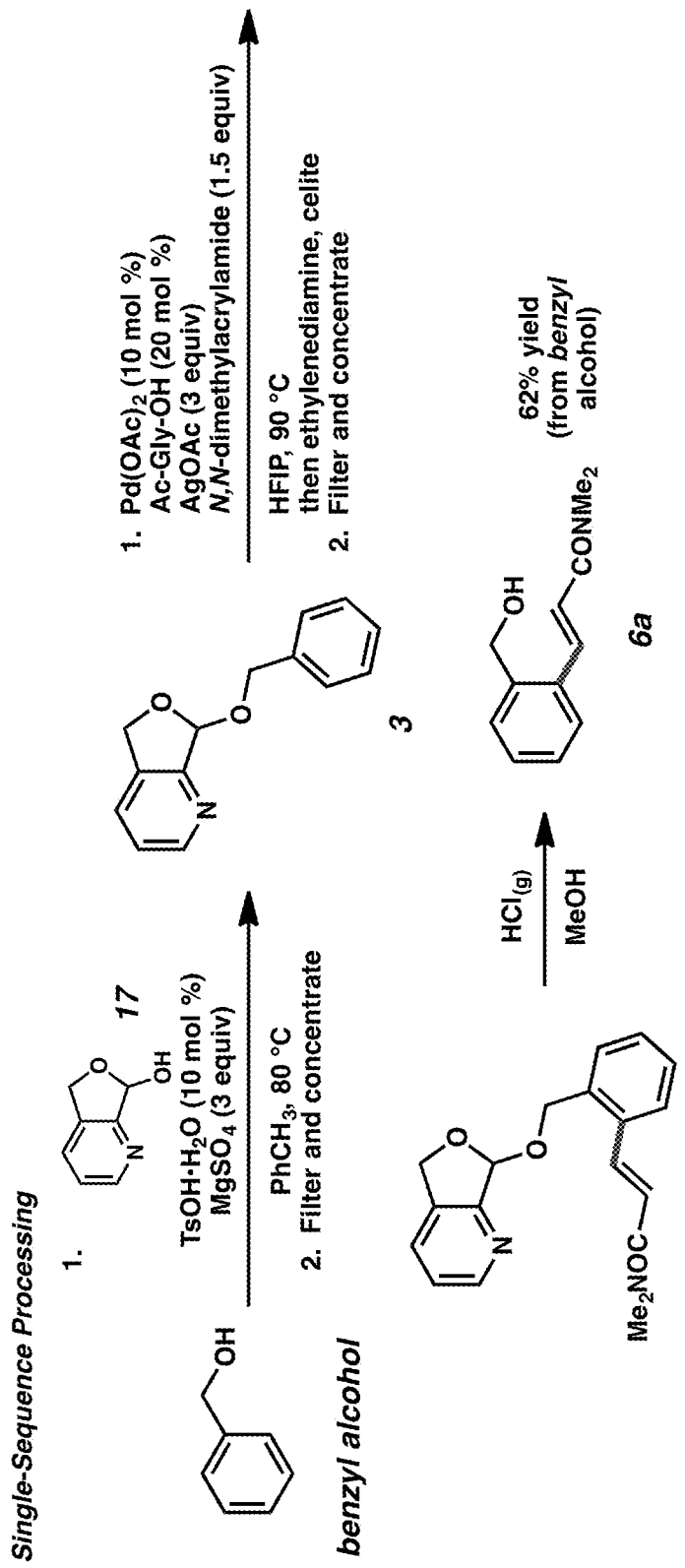
FIG. 3 illustrates Scheme 3.

In another embodiment, as shown in Scheme 3 (FIG. 3), the reaction sequence or process may be effected without isolation of any products. For example, Compound 6a was synthesized in the same manner as in Scheme 1 (FIG. 1) without purification of compound 3 or compound 5a to provide a 42% yield of compound 6a.

In another embodiment, the scaffold compound 2 may be recovered. Benzylic alcohol 9 was coupled with alkene 18 in the presence of $Pd(OAc)_2$ to provide compound 19. Compound 19 was treated with gaseous hydrogen chloride in methanol to yield alcohol 20 and compound 2 in high yields.

Example 3

Reaction of Phenyl-BPin (Table 1):

Reaction of one equivalent of 2-methylbenzylOPyA with PhBPin (3 equiv) under the catalysis of $Pd(OAc)_2$ (10 mol %) and Ac-Gly-OH (20 mol %), $Ag_2CO_3$ (1 equiv) and CsF (2 equiv) as the additives in HFIP (0.1 M) at 90° C. for 6 h, the desired product was afforded in 11% NMR yield, with 83% NMR yield of rsm (entry 1, Table 1).

TABLE 1

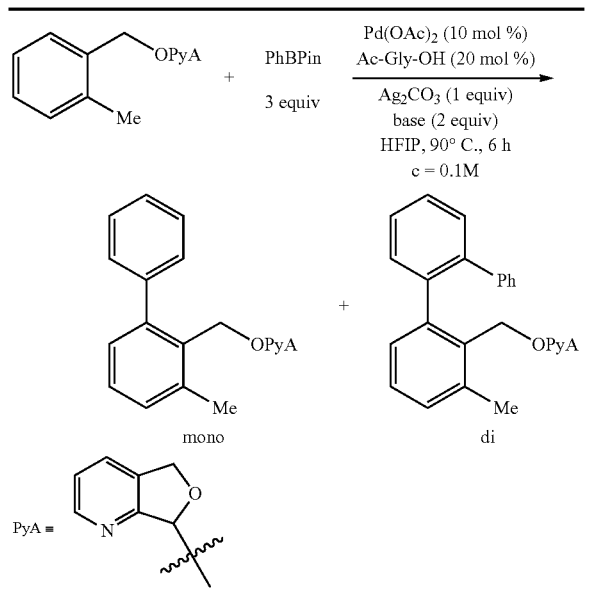

TABLE 2[a]

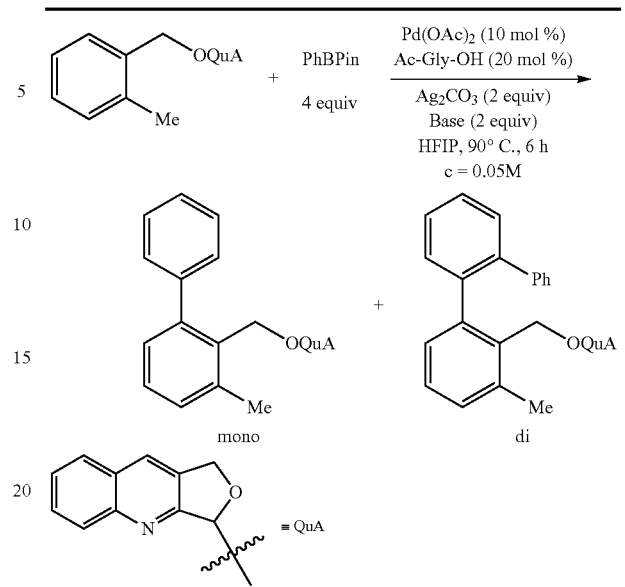

| entry | Base | Yield[a] (mono/di %) | rsm[a] (%) | No. |
|---|---|---|---|---|
| 1 | CsF | 11 | 83 | 3-41 |
| 2[b] | CsF | NR | — | 3-43 |
| 3 | NaOAc | trace | — | 4-1 |
| 4 | KOAc | 5 | 85 | 3-48 |
| 5 | $K_2CO_3$ | 21 | 70 | 3-42 |
| 6 | $Cs_2CO_3$ | 20/trace | 71 | 3-96 |
| 7 | $Na_3PO_4$ | 31/trace | 69 | 3-100 |
| 8 | $Na_2CO_3$ | 34/3 | 51 | 3-95 |
| 9[c] | $Na_2CO_3$ | 37/2 | 52 | 4-6 |
| 10[c,d] | $Na_2CO_3$ | 39/1 | 58 | 4-11 |
| 11[c,e] | $Na_2CO_3$ | 40/3 | 47 | 4-12 |
| 12[c,f] | $Na_2CO_3$ | 30/3 | 64 | 4-15 |
| 13[c,e,g] | $Na_2CO_3$ | 29 | 69 | 4-17 |
| 14[c,e,h] | $Na_2CO_3$ | 43/4 | 38 | 4-18 |
| 15[c,e,i] | $Na_2CO_3$ | 33/1 | 50 | 4-34 |
| 16[c,e,h,j] | $Na_2CO_3$ | 46/5 | 35 | 4-19 |

[a]NMR yield with 1-octene as the internal standard;
[b]DCE as the solvent;
[c]$Ag_2CO_3$ (2 equiv);
[d]$Na_2CO_3$ (4 equiv);
[e]$Na_2CO_3$ (1 equiv);
[f]$Na_2CO_3$ (0.5 equiv);
[g]c = 0.2M;
[h]c = 0.05M;
[i]c = 0.033M;
[j]15 hours.

Then $Na_2CO_3$ (2 equiv) gave the best result (34/3% mono/di, 51% rsm, entry 8, Table 1) among different bases. Reagent ratio and concentration shows that more oxidants (2 equiv), less base (1 equiv), and less concentration (0.05 M) gave a better result (43/4% mono/di, 38% rsm, entries 9-15, Table 1).

Figure 4:
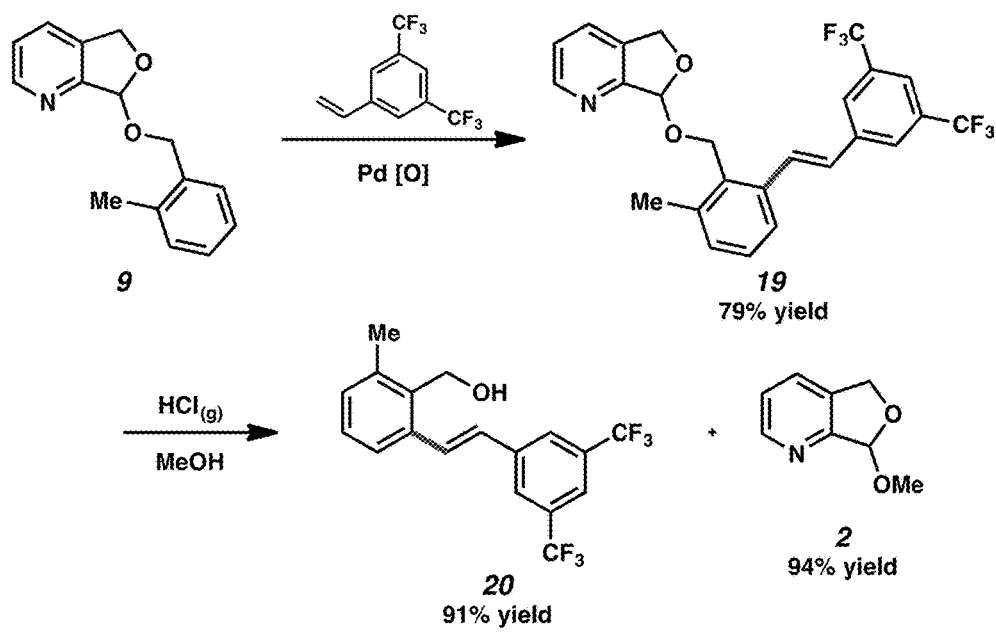
FIG. 4 illustrates Scheme 4.
Figure 5:
FIG. 5 illustrates Scheme 5.
Figure 6B:
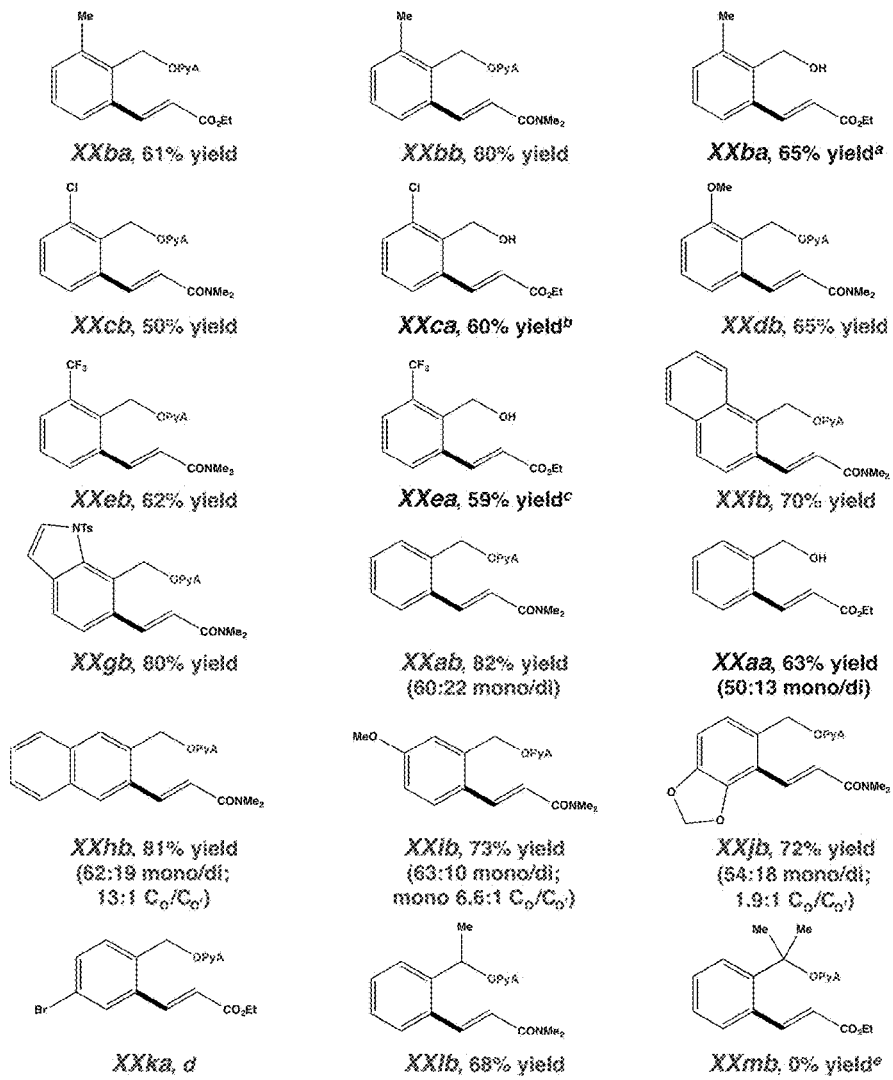

Other embodiments are provided in the examples of Schemes 4 and 6a (FIGS. 4 and 6).

Example 4

The residue QuA was prepared and attached to 2-methyl benzyl alcohol according to Scheme 7 (FIG. 7).

Example 5

When the QuA-attached benzyl alcohol was subjected to the coupling reaction (see substantially same conditions of Example 3), higher yield (69% NMR yield of mono) was achieved (entry 1, Table 2).

| Entry | Base | Yield[b] (mono/di) (%) | rsm[b] (%) | No. |
|---|---|---|---|---|
| 1 | $Na_2CO_3$ | 77 (69/8) | 17 | 6-26 |
| 2 | $Na_3PO_4$ | 79 (71/8) | 17 | 6-43 |
| 3 | $KHCO_3$ | 86 (75/11) | 7 | 6-44 |
| 4 | $K_2CO_3$ | 89 (75/14) | 6 | 6-45 |
| 5 | $K_3PO_4$ | 52 (50/2) | 47 | 6-60 |
| 6 | $Cs_2CO_3$ | 87 (75/12) | 9 | 6-61 |
| 7[c] | $K_2CO_3$ | 76 (67/9) | 23 | 6-62 |
| 8[d] | $K_2CO_3$ | 88 (74/14) | 6 | 6-65 |
| 9[e] | $K_2CO_3$ | 87 (77/10) | 10 | 6-67 |
| 10[f] | $K_2CO_3$ | 59 (57/2) | 39 | 6-74 |
| 11[g] | $K_2CO_3$ | 18 (18/0) | 76 | 6-75 |
| 12[h] | $K_2CO_3$ | 86 (74/12) | 9 | 6-76 |
| 13[i] | $K_2CO_3$ | 85 (77/8) | 8 | 6-63 |
| 14[j] | $K_2CO_3$ | 76 (70/6) | 16 | 6-64 |
| 15[k] | $K_2CO_3$ | 83 (75/8) | 10 | 6-91 |
| 16[l] | $K_2CO_3$ | 89 (84/5) | 7 | 7-73 |
| 17[m] | $K_2CO_3$ | 77 (76/1) | 17 | 6-95 |

[a]Reaction conditions: XX (0.1 mmol), PhBPin (4.0 equiv), $Pd(OAc)_2$ (10 mol %), Ac-Gly-OH (20 mol %), $Ag_2CO_3$ (2.0 equiv), base (2.0 equiv) in HFIP (2 mL), 90° C., 6 h;
[b]NMR yield with 1-octene as the internal standard;
[c]5 mol % of $Pd(OAc)_2$ for 12 h;
[d]10 h;
[e]reaction at 70° C. for 12 h;
[f]$PhBF_3K$ instead of PhBPin;
[g]0.5 equiv of benzoquinone was added;
[h]2 equiv of water was added;
[i]Ac-Val-OH as the ligand;
[j]Ac-Ala-OH as the ligand;
[k]Ac-Leu-OH as the ligand;
[l]Ac-Ile-OH as the ligand;
[m]Ac-tert-Leu-OH as the ligand.

Interestingly, a second arylation of the new formed phenyl group could be afforded in 8% NMR yield, plus 17% rsm. After screening of different bases, $K_2CO_3$ (2 equiv) gave the best yield (75/14% mono/di, 6% rsm, entry 4, Table 2). Less amount of $Pd(OAc)_2$ (5 mol %) or lower temperature both led to decreased yields even with longer reaction time (entry 7, 9, Table 2). $PhBF_3K$ showed lower reactivity than PhBPin (entry 10, Table 1). Benzoquinone and water, which were supposed to increase the reduction elimination rates, did not show any advantages in this chemistry (entry 11, 12, Table 2).

In studies on the effects of the ligands, Ac-Ile-OH turned out to be the best one (with a much better mono/di ratio, entry 16, Table 2). Ac-tert-Leu-OH gave the best mono/di ratio, but lower yield (entry 17, Table 2). Apparently bulky ligand can control the form of the di-product, but lead to a lower yield. Finally we chose entry 16 in Table 2 as the optimized conditions for further studies.

Figure 8:
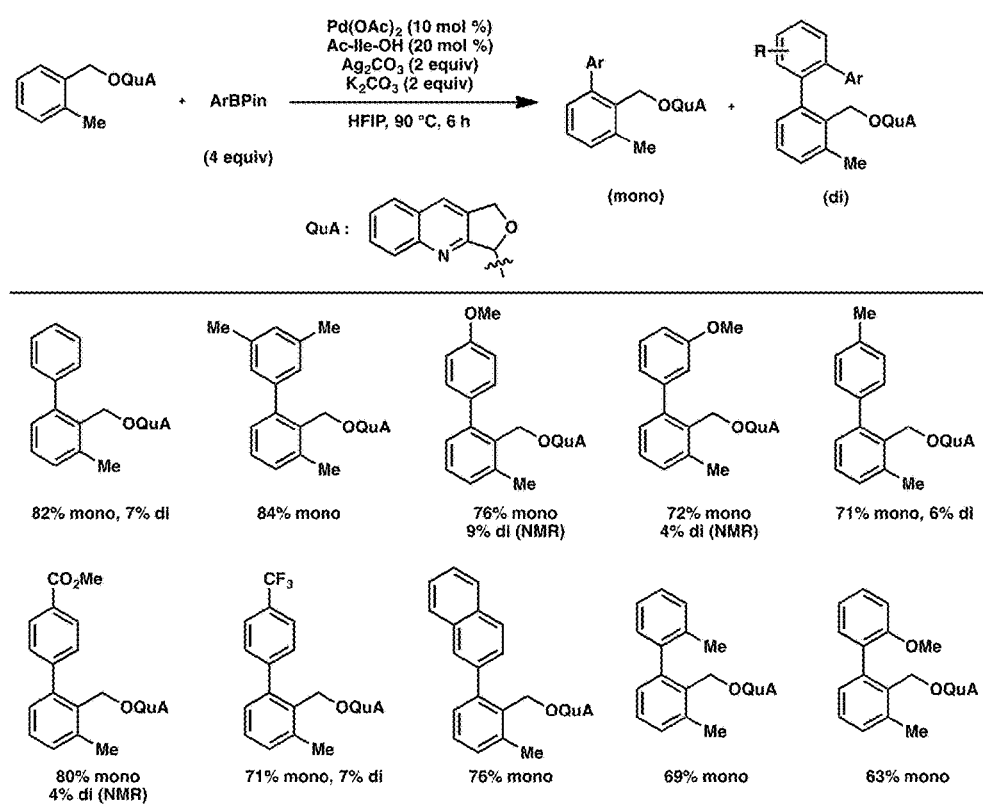
Figure 9:
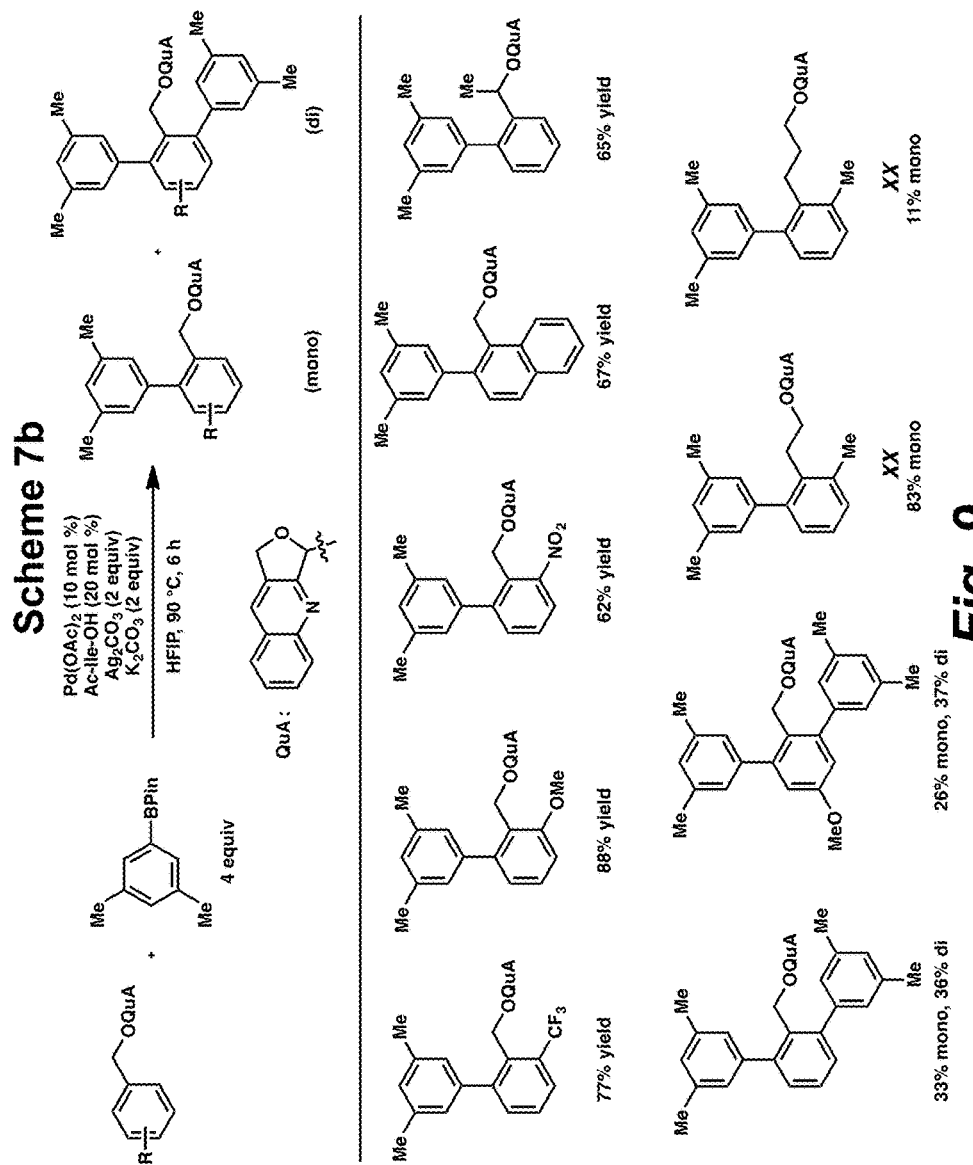
FIG. 9 illustrates Scheme 7b.

With reference to Schemes 7a and 7b (FIGS. 8 and 9), the aryl group coupled may be substituted. Various substituted Ar-BPins (both electro-donating and electro-withdrawing substituted groups, such as OMe, $CF_3$, $CO_2Me$) were tolerated, affording the corresponding products in good to excellent yields. Moreover, 2-naphthylboronic acid pinacol ester was also tolerated, gave the corresponding mono product in 76% yield. Gratifyingly, ortho-substituents Ar-BPins still gave a good yield. Then a range of scaffold-attached benzylic alcohol substrates were evaluated. For ortho-substituted arenes, moderate to good yields of the biaryls were formed. For cases without substituted groups at the ortho-position, both mono- and di-biaryls were observed. Homobenzyl alcohol was tolerated in this transformation, affording the corresponding product in 83% yield. But bishomobenzylic alcohol substrate shows low reactivity with only 11% NMR yield, plus 77% rsm. A secondary alcohol-based substrate was reactive, which shows mono-selectivity.

With reference to Scheme 8 (FIG. 10), two steps with only one purification gave the biaryl alcohol in 89% yield, with the scaffold recovered in 86% yield, highlighting the utility of this scaffold. Furthermore, benzylic alcohol could be converted to the arylation product without any intermediary purification (59% yield, 35% rsm of benzylic alcohol, 73% recovery of the scaffold based on BzOQuA), but for the arylation step, reaction was failed to go completion, probably due to the quinoline-based impurities from the first step.

Therefore, although selected aspects have been illustrated and described in detail, it will be understood that various substitutions and alterations may be made therein without departing from the spirit and scope of the present invention, as defined by the following claims.

We claim:

1. A method for the ortho-arylation of a benzylic alcohol, comprising the steps of:

(a) generating a quinolinyl hemiacetal benzoate scaffold having the formula II;

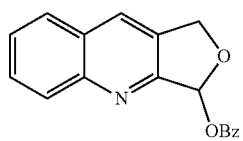

II (b) reacting a benzylic alcohol of formula I

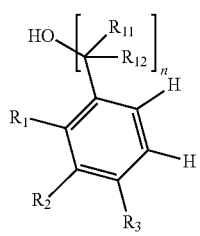

I with the quinolinyl hemiacetal benzoate scaffold of formula II in the presence of trifluoroacetic acid to provide a compound of formula III:

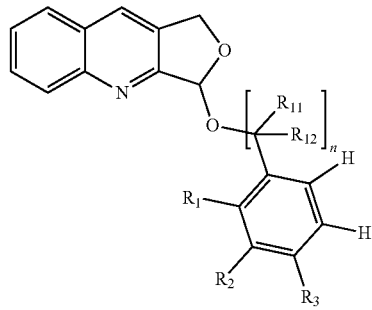

III (c) reacting the compound of formula III with an arylboronic pinacol ester having the formula IVa:

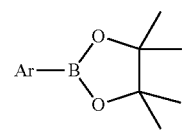

IVa in the presence of a palladium acetate, rhodium acetate, or ruthenium acetate catalyst; an N-acetylated amino acid metal catalyst ligand selected from the group consisting of Ac-Glycine-OH, Ac-Valine-OH, Ac-Alanine-OH, Ac-Leucine-OH, Ac-Isoleucine-OH, and Ac-tert-butylleucine-OH; a silver salt; and a base selected from the group consisting of: $Na_2CO_3$, $KHCO_3$, $K_2CO_3$, $K_3PO_4$, and $Cs_2CO_3$ to provide a compound of formula Va:

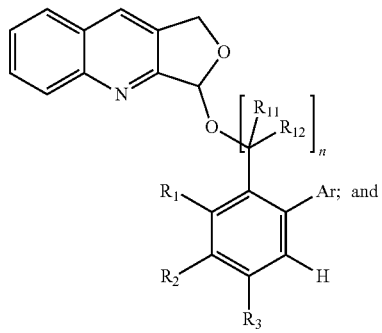

Va (d) reacting the compound formula Va of step (c) with an acid and an alcohol, said alcohol having the formula $R_{13}OH$ to provide an ortho-arylated benzylic alcohol of formula VIa

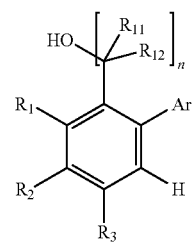

VIa and a quinolinyl hemiacetal alkoxy scaffold having the formula VII;

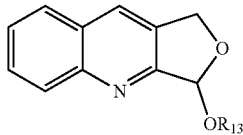

wherein
- $R_1$, $R_2$, and $R_3$ are independently selected from the group consisting of: hydrogen, an alkyl, an aryl, $R_1$ and $R_2$ forming an aryl ring, and $R_2$ and $R_3$ forming an aryl ring;
- $R_{11}$ and $R_{12}$ are independently hydrogen or an alkyl; and $R_{13}$ is an alkyl or substituted alkyl;
- Ar is an unsubstituted or substituted aryl; and
- n is 1 or 2.

2. The method of claim 1 wherein, when $R_1$ and $R_2$ of the benzylic alcohol having the formula I are both hydrogen, the compound having formula VIa is diarylated and $R_1$ of the compound VIa is an aryl.

3. The method of claim 1, further comprising repeating steps (b)-(d), wherein the quinolinyl hemiacetal alkoxy scaffold VII released in step (d) reacts with the benzylic alcohol I in step (b) to further generate compound III.

4. The method of claim 1, wherein the method further comprises the step of isolating the ortho-arylated benzylic alcohol of formula VIa.

5. The method of claim 1, wherein the catalyst is palladium acetate ($Pd(OAc)_2$).

6. The method of claim 1, wherein the N-acetylated amino acid metal catalyst ligand is Ac-Isoleucine-OH.

7. The method of claim 1, wherein the silver salt is silver carbonate $Ag_2CO_3$.

8. The method of claim 1, wherein the base is $K_2CO_3$.

9. The method of claim 1, wherein the Ar is an aryl group having at least one substituent group, wherein each at least one substituent group is independently selected from the group consisting of an alkyl, an alkoxy, an halogenated alkyl, and an alkoxycarbonyl.

10. The method of claim 9, wherein the aryl group has at least one substituent group, wherein each substituent is an alkyl.

11. The method of claim 10, wherein the aryl group has at least one substituent group, wherein each substituent is a methyl.

12. The method of claim 1, wherein step (c) is in the presence of palladium acetate ($Pd(OAc)_2$), Ac-Isoleucine-OH, silver carbonate ($Ag_2CO_3$), and $K_2CO_3$.

* * * * *